United States Patent
Borchert et al.

(10) Patent No.: US 6,670,504 B1
(45) Date of Patent: Dec. 30, 2003

(54) METHOD AND PRODUCING ACETIC ACID IN A REACTOR CASCADE

(75) Inventors: Holger Borchert, Bockenheim (DE); Uwe Dingerdissen, Seeheim-Jugenheim (DE); Ranier Roesky, Frankfurt am Main (DE)

(73) Assignee: Hoechst Research & Technology Deutschland GmbH & Co. KG (DE)

( * ) Notice: Subject to any disclaimer, the term of this patent is extended or adjusted under 35 U.S.C. 154(b) by 0 days.

(21) Appl. No.: 09/403,517
(22) PCT Filed: Apr. 11, 1998
(86) PCT No.: PCT/EP98/02126
§ 371 (c)(1), (2), (4) Date: Nov. 10, 1999
(87) PCT Pub. No.: WO98/47851
PCT Pub. Date: Oct. 29, 1998

(30) Foreign Application Priority Data

Apr. 23, 1997 (DE) .......................... 197 17 075

(51) Int. Cl.[7] .............. C07C 51/16; B01J 23/00
(52) U.S. Cl. ...................... 562/549; 502/313
(58) Field of Search .............. 562/549; 502/313

(56) References Cited

U.S. PATENT DOCUMENTS 5,300,684 A * 4/1994 Benkalowycz et al.

* cited by examiner

Primary Examiner—Johann Richter
Assistant Examiner—Paul A. Zucker
(74) Attorney, Agent, or Firm—Bierman, Muserlian and Lucas

(57) ABSTRACT

The invention relates to a method for producing acetic acid from ethane and oxygen on a fixed bed catalyst, characterized in that a reactor cascade with an oxygen feed between the reactor levels is used. This particularly advantageous method provides high conversion rates, highly pure acetic acid and low ethylene and carbon monoxide formation.

13 Claims, 1 Drawing Sheet

METHOD AND PRODUCING ACETIC ACID IN A REACTOR CASCADE

Figure 1:
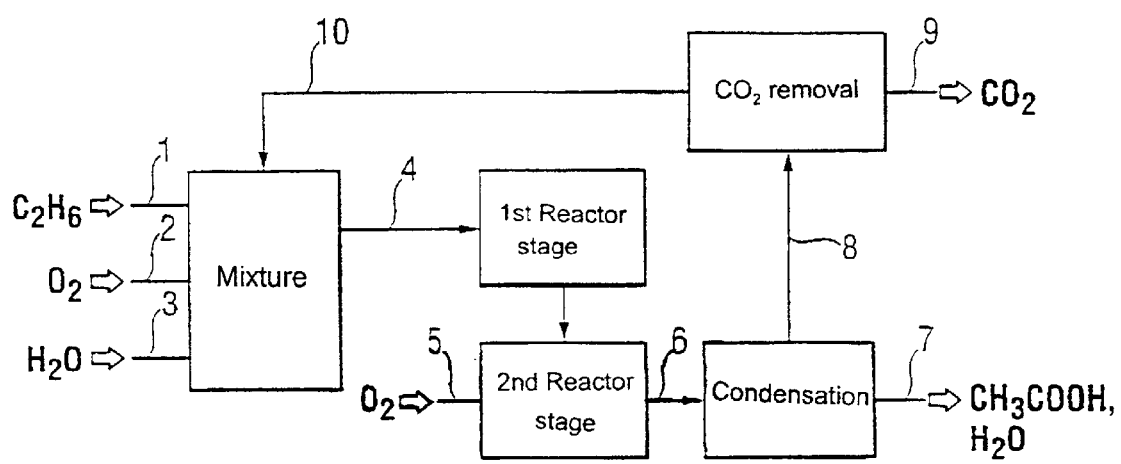

This application is a 371 of PCT/EP98/02126 filed Apr. 11, 1998.

The present invention relates to an improved process for the preparation of acetic acid by oxidation of ethane by carrying out the reaction in a reactor cascade.

Catalytic gas-phase oxidation of ethane to ethylene and acetic acid is known. In 1978, the Union Carbide Corporation published a report in the Journal of Catalysis 52, 116–132, in which catalysts for the oxidative dehydrogenation of ethane to ethylene are described. Several U.S. patents (U.S. Pat. Nos. 4,250,346, 4,524,236, 4,568,790, 4,899,003 and 4,598,787) have been granted for processes which relate to the oxidative dehydrogenation of ethane to ethylene at low temperatures. Possibly, commercializable processes for the oxidative dehydrogenation of ethane to ethylene are disclosed in The Arabian Journal for Science and Engineering 1985, I10, 353–360, U.S. Pat. No. 4,899,003 and EP-A-0 261 264. Acetic acid is formed only as byproduct in these processes.

A process for the conversion of ethane to acetic acid is essentially determined by the reaction conditions necessary for a maximum yield of acetic acid based on the starting material ethane. As disclosed in EP-A-0 407 09, the conversion is carried out in the gas phase at temperatures between 200 and 500° C. and under an elevated pressure of up to 30 bar. To avoid explosive gas mixtures, ethane is fed into the reactor in excess relative to the amount of oxygen. This means that the ethane conversion and the amount of acetic acid which can be achieved for each passage through the reactor is limited by the oxygen concentration in the gas entering the reactor. In addition, steam is fed into the gas entering the reactor, which has the advantage that the formation of acetic acid is favored at the expense of ethylene formation. The disadvantage is that this results in a dilute aqueous acidic acid, with the consequence that the costs for working up to concentrated acetic acid are considerable.

A process for the oxidation of ethane to acetic acid is disclosed in U.S. Pat. No. 5,300,684. This process comprises feeding ethane and a recycled gas into a fluidized bed reaction zone containing fluidized particles of solid oxidation catalyst, and feeding in a molecular oxygen-containing gas separately from the ethane input. The gaseous byproducts formed in the process are ethylene, carbon dioxide and carbon monoxide. The process therefore also includes the stages of 1) Cooling the gaseous product which has been stripped out of the reaction zone,
2) Removing most of the acetic acid in liquid form from the outflowing gases, and
3) Discharging a part-stream from the recycled gas.

The advantages mentioned for the fluidized bed reactor are:

1. Because of the hydrodynamics of the fluidized bed reactor, the back-mixing of the gas in the reactor is favored and thus the selectivity for acetic acid is favored at the expense of ethylene formation.
2. The mixing of the reactive gases ethane and oxygen with the inert reaction product carbon dioxide allows higher concentrations of oxygen in the entering gas to be used in a fluidized bed reactor than in a fixed bed reactor. This achieves a higher ethane conversion for each passage through the reactor.

However, the fluidized bed reactor has the following disadvantages, according to Fluidization Engineering, Butterworth Heinemann, Boston, 1991, p. 10:

1. The back-mixing of the reaction gas in the fluidized bed reactor leads to a reduction in yield due to further oxidation of the required products (in this case acetic acid) to carbon dioxide and carbon monoxide.
2. The catalyst costs are high because of the great mechanical abrasion of the catalyst.

The discharge of the part-stream from the recycled gas disclosed in U.S. Pat. No. 5,300,684 is intended to prevent enrichment of carbon dioxide in the reactor gas. The advantage mentioned for the discharge is that this avoids the cryogenic removal of carbon monoxide and ethylene, which is costly in energy terms. However, it has the disadvantage that there is discharge not only of carbon dioxide, carbon monoxide and ethylene but also of part of the unreacted ethane. The loss of the valuable raw material ethane results in considerably higher material costs relative to the amount of acetic acid formed.

Another disadvantage of the process is that the aqueous acetic acid is formed in highly dilute form. It is evident from the example disclosed in U.S. Pat. No. 5,300,684 that the acetic acid concentration is only 26 percent by weight, so that the costs of working up to concentrated acetic acid are considerable.

The object therefore was to provide a process which permits acetic acid to be obtained economically by catalytic oxidation of ethane.

It has been found, surprisingly, that the disadvantages of the prior art processes are avoided if the oxidation of ethane to acetic acid is carried out in a reactor cascade.

The invention relates to a process for the preparation of acetic acid from ethane and oxygen or oxygen-containing gases on a fixed bed catalyst, which comprises a) feeding ethane, oxygen or an oxygen-containing gas and a recycled gas into a reactor which contains a fixed bed catalyst,
b) mixing the reactor exit gas obtained in step a) with oxygen or an oxygen-containing gas without removing water or acetic acid beforehand,
c) feeding the gas mixture obtained in step b) into another reactor which contains a fixed bed catalyst,
d) cooling the reactor exit gas obtained in step c),
e) removing all or part of the carbon dioxide present in the gas stream obtained in step d), and
f) using the gas stream obtained in step e) as recycled gas for step a).

For illustration, a process flow diagram depicting a two-stage reaction as example is shown in FIG. 1. The individual process steps in the process according to the invention are described in detail hereinafter.

The gas entering the reactor is obtained by mixing a recycled gas which consists predominantly of unreacted ethane and carbon dioxide with fresh ethane and oxygen or a molecular oxygen-containing gas, and feeding the mixture into a fixed bed reactor. The oxygen-containing gas may be air or a gas which has a higher or lower oxygen content than air. It is advantageous to use pure oxygen because, in this case, the cryogenic removal of nitrogen from the reaction gas is unnecessary. The entering gas may additionally comprise steam in concentrations of from 1 to 50% by volume. A steam concentration of from 5 to 30% by volume is preferred. The addition of steam makes a higher selectivity in the formation of acetic acid possible. The molar ratio of total ethane to oxygen fed into the reaction zone is preferably in the range between 2:1 and 10:1, in particular between 3:1 and 8:1.

The entering gas is passed through a reactor in which the catalyst is arranged as fixed bed. Ethane is oxidized to acetic acid by catalytic oxidation, with suitable choice of the catalyst and of the reaction conditions resulting in the formation only of carbon dioxide predominantly as byproduct, and there being no formation of other gaseous products such as ethylene and carbon monoxide. The reaction is carried out at temperatures between 150 and 500° C., preferably 200 to 400° C. The pressure can be atmospheric or superatmospheric and preferably be in the range between 1 and 50 bar, in particular 2 to 30 bar. The residence time in the reactor is adjusted so that relatively substantial oxygen conversion is achieved. It is preferable to use as catalyst the catalysts described in German Patent Applications 19630832.1 or 19620542.5, which are incorporated herein by reference.

DE-19620542.5 discloses a catalyst which comprises the elements Mo, Pd, Re, X and Y in the gram-atom ratios a:b:c:d:e in combination with oxygen

and the symbols X and Y have the following meaning:

X=Cr, Mn, Nb, B, Ta, Ti, V and/or W

Y=Bi, Ce, Co, Te, Fe, Li, K, Na, Rb, Be, Mg, Ca, Sr, Ba, Ni, P, Pb, Sb, Si, Sn, Ti and/or U. The indices a, b, c, d and e are the gram-atom ratios of the appropriate elements, where a=1, b=0.0001–0.5, c=0.25–1.0

DE-19630832.1 discloses a catalyst which comprises the elements Mo, Pd, X and Y in the gram-atom ratios a:b:c:d in combination with oxygen

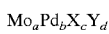

and the symbols Z and Y have the following meaning:

X=Cr, Mn, Nb, Ta, Ti, V, Te and/or W

Y=B, Al, Ga, In, Pt, Zn, Cd, Bi, CeCo, Cu, Rh, Ir, Au, Ag, Fe, Ru, Os, K, Rb, Cs, Mg, Ca, Sr, Ba, Zr, Hf, Ni, P, Pb, Sb, Si, Sn, Ti, and/or U. The indices a, b, c and d are the gram-atom ratios of the appropriate elements, where a=1 b=0.0001–0.5, c=0.1–1.0

It is also possible to use for the process according to the invention a tungsten-containing catalyst which comprises the elements W, X, Y and Z in the gram-atom ratios a:b:c:d in combination with oxygen

in which X is one or more elements selected from the group of Pd, Pt, Ag and/or Au, Y is one or more elements selected from the group of V, Nb, Cr, Mn, Fe, Sn, Sb, Cu, Zn, U, Ni and/or Bi, Z is one or more elements selected from the group of Li, Na, K, Rb, Cs, Be, Mg, Ca, Sr, Ba, Sc, Y, La, Ti, Zr, Hf, Ru, Os, Co, Rh, Ir, B, Al, Ga, In, Tl, Si Ge, Pb, P, As and/or Te, a is 1, b is a number greater than 0, c is a number greater than 0, and d is a number from 0 to 2.

The selectivity of the oxidation of ethane to acetic acid when carrying out the process according to the invention is $\geq 60$ mol %, preferably $\geq 75$ mol %, in particular $\geq 80$ mol %, with an ethane conversion per reactor stage of >4%, preferably >5%, in particular >6%. Another advantage of the process is that there is virtually exclusive formation of carbon dioxide as byproduct, while the formation of ethylene or carbon monoxide is negligible. The total of the selectivities for the production of ethylene and carbon monoxide is $\leq 5$ mol %, preferably $\leq 4$ mol %, in particular $\leq 3$ mol %.

The reactor exit gas leaving the first reactor stage is mixed with oxygen or an oxygen-containing gas and, without previously condensing out water and acetic acid, passed into a second reactor. The use of several reactor stages arranged in succession, with oxygen-containing gas being fed in between the reactor stages without removing the acetic acid, makes a high ethane conversion possible and reduces the amount of gas recycled. The aqueous acetic acid obtained after the last reactor stage has a higher concentration than in a one-stage reactor. This considerably simplifies the working up to concentrated acetic acid. The number of reactor stages depends on the ethane and oxygen conversions achieved in the individual stages. It is preferably $\geq 2$ stages. Increasing the number of reactor stages achieves an increase in the ethane conversions and a reduction in the amount of gas recycled. In addition, the concentration of the aqueous acetic acid increases after the last reactor stage. On the other hand, however, the costs for the reactors increase. This means that it is necessary, from the viewpoint of economy, to optimize the number of reactor stages as a function of the ethane and oxygen conversions achieved in the reactor stages.

On use of the abovementioned catalysts, the acetic acid formed in the first reactor stage is not oxidized further in the subsequent reactor stages. It is therefore unnecessary to remove the acetic acid by condensation from the gas stream after the individual stages.

After the last reactor stage, the reactor exit gas is cooled, with water and the acetic acid formed condensing out. The gas stream obtained after the condensation consists mainly of ethane and carbon dioxide plus very small amounts of ethylene and carbon monoxide.

The carbon dioxide formed during the reaction is removed from the gas stream by washers or membranes in order to avoid its accumulation in the circulating gas. Carbon dioxide is preferably removed by washing. Only ethane and the remaining amount of carbon dioxide plus small amounts of ethylene and carbon monoxide then remain in the circulating gas.

The negligible formation of ethylene and carbon monoxide when the process according to the invention is carried out means that the cryogenic removal of these gases, which is costly in energy terms, from unreacted ethane is unnecessary. Likewise, the discharge of a part-stream from the recycled gas, described in U.S. Pat. No. 5,300,684, is unnecessary. This avoids a loss of valuable ethane.

After removal of the carbon dioxide formed in the reaction, the circulating gas is recycled to the first reactor inlet, mixed with fresh ethane, oxygen and steam, and fed again into the first reactor stage.

EXAMPLE

A specific example is compiled in Table 1, where the identifications of the quantity flows are the same as in FIG. 1. In this example, the temperature in the reactor stages is about 280° C. and the pressure is about 15 bar. The catalyst used contains the elements Mo, Pd, V, Nb, Sb and Ca ($Mo_aPd_bV_cNb_dSb_eCa_f$) in the gram-atom ratios a:b:c:d:e:f= 1:0.0005:0.36:0.03:0.01:0.01 in combination with oxygen. It is to be noted that the yield of acetic acid based on ethane freshly fed in is very high because no discharge of ethane-containing gas from the recycled stream is carried out. In addition, the concentration of the aqueous acetic acid produced is very high at 45% by weight.

TABLE 1

Quantity flows for the process flow diagram (FIG. 1)

Quantity flows in 1000 kg/hour

| Substance | 1 | 2 | 3 | 4 | 5 | 6 | 7 | 8 | 9 | 10 |
|---|---|---|---|---|---|---|---|---|---|---|
| $C_2H_6$ | 19.6 | 0 | 0 | 77.3 | 0 | 60.0 | 0.2 | 59.9 | 0 | 68.0 |
| $O_2$ | 0 | 15.3 | 0 | 33.0 | 15.3 | 2.4 | 0 | 2.4 | 0 | 2.4 |
| $H_2O$ | 0 | 0 | 26.3 | 26.3 | 0 | 38.5 | 37.9 | 0.6 | 0.6 | 0 |
| $CH_3COOH$ | 0 | 0 | 0 | 0 | 0 | 31.3 | 30.7 | 0.5 | 0.5 | 0 |
| $CO_2$ | 0 | 0 | 0 | 103.0 | 0 | 107.7 | 0.3 | 107.3 | 4.6 | 103.0 |

What is claimed is:

1. A process for the preparation of acetic acid from ethane and oxygen or oxygen-containing gases on a fixed bed catalyst, which comprises
   a) feeding ethane, oxygen or an oxygen-containing gas and a recycled gas into a reactor which contains a fixed bed catalyst,
   b) mixing the reactor exit gas obtained in step a) with oxygen or an oxygen-containing gas without removing water or acetic acid beforehand,
   c) feeding the gas mixture obtained in step b) into another reactor which contains a fixed bed catalyst,
   d) cooling the reactor exit gas obtained in step c),
   e) removing all or part of the carbon dioxide present in the gas stream obtained in step d), and
   f) using the gas stream obtained in step e) as recycled gas for step a).

2. The process as claimed in claim 1, wherein the reactor exit gas obtained in step c) is, before the cooling in step d), fed into one or more other reactors and, before each feeding in, the reactor exit gas is mixed with oxygen or oxygen-containing gases.

3. The process as claimed in claim 1, wherein the gas entering the reactor comprises 1 to 50% by volume of steam.

4. The process as claimed in claim 1, wherein the molar ratio of ethane to oxygen in the gas entering the reactor is between 2:1 and 10:1.

5. The process as claimed in claim 1, wherein the reaction is carried out at temperatures between 150 and 500° C.

6. The process as claimed in claim 1, wherein the reaction is carried out under pressures between 1 and 50 bar.

7. The process as claimed in claim 1, wherein a catalyst which comprises the elements Mo, Pd, Re, X and Y in the gram-atom ratios a:b:c:d:e in combination with oxygen $$Mo_aPd_bRe_cX_dY_e$$

wherein the symbols X and Y mean
   X=Cr, Mn, Nb, B, Ta, Ti, V and/or W,
   Y=Bi, Ce, C, Te, Fe, Li, K, Na, Rb, Be, Mg, Ca, Sr, Ba, Ni, P, Pb, Sb, Si, Sn, Tl and/or U,
   and the indices a, b, c, d and e are the gram-atom ratios of the appropriate elements, wherein a=1, b=0.0001–0.5, c=0.25–1.0.

8. The process as claimed in claim 1, wherein a catalyst which comprises the elements Mo, Pd, X and Y in the gram-atom ratios a:b:c:d in combination with oxygen $$Mo_aPd_bX_cY_d$$

wherein the symbols X and Y mean
   X=Cr, Mn, Nb, Ta, Ti, V, Te and/or W,
   Y=B, Al, Ga, In, Pt, n, Cd, Bi, Ce, Co, Cu, Rh, Ir, Au, Ag, Fe, Ru, Os, K, Rb, Cs, Mg, Ca, Sr, Ba, Zr, Hf, Ni, P, Pb, Sb, Si, Sn, Ti, and/or U, and the indices a, b, c and d are the gram-atom ratios of the appropriate elements, wherein a=1, b=0.0001–0.5, c=0.1–1.0.

9. The process as claimed in claim 1, wherein a tungsten-containing catalyst which comprises the elements W, X, Y and Z in the gram-atom rations a:b:c:d in combination with oxygen $$W_aX_bY_cZ_d(I)$$

in which
   X is one or more elements selected from the group of Pd, Pt, Ag and/or Au,
   Y is one or more elements selected from the group of V, Nb, Cr, Mn, Fe, Sn, Sb, Cu, Zn, U, Ni and/or Bi,
   Z is one or more elements selected from the group of Li, Na, K, Rb, Cs, Be, Mg, Ca, Sr, Ba, Sc, Y, La, Ti, Zr, Hf, Ru, Os, Co, Rh, Ir, B, Al, Ga, In, Tl, Si, Ge, Pb, P, As and/or Te,
   a is 1,
   b is a number greater than 0,
   c is a number greater than 0, and
   d is a number from 0 to 2, is used.

10. The process of claim 1 wherein the gas entering the reactor comprises 5 to 50% by volume of steam.

11. The process of claim 1 wherein the molar ratio of ethane to oxygen in the gas entering the reaction is between 3:1 and 8:1.

12. The process of claim 1 wherein the reaction is carried out at a temperature of 200 to 400° C.

13. The process of claim 1 wherein the reaction is carried out at a pressure of between 2 and 30 bar.

* * * * *